(12) United States Patent
Cinader, Jr.

(10) Patent No.: US 7,473,096 B2
(45) Date of Patent: Jan. 6, 2009

(54) ORTHODONTIC ADHESIVE DISPENSING ASSEMBLY

(75) Inventor: David K. Cinader, Jr., Yorba Linda, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 11/425,461

(22) Filed: Jun. 21, 2006

(65) Prior Publication Data

US 2007/0298364 A1   Dec. 27, 2007

(51) Int. Cl.
*A61C 3/00* (2006.01)
(52) U.S. Cl. .................... 433/3; 433/9; 433/24
(58) Field of Classification Search .......... 433/2, 433/3, 8, 9, 24, 213
See application file for complete search history.

(56) References Cited

U.S. PATENT DOCUMENTS

| | | | | |
|---|---|---|---|---|
| 4,551,096 | A * | 11/1985 | Dellinger | 433/24 |
| 5,008,304 | A * | 4/1991 | Kmentt | 523/118 |
| 5,152,917 | A | 10/1992 | Pieper et al. | |
| 5,500,273 | A | 3/1996 | Holmes et al. | |
| 5,552,177 | A | 9/1996 | Jacobs et al. | |
| 5,575,645 | A * | 11/1996 | Jacobs et al. | 433/9 |
| 5,890,892 | A * | 4/1999 | Lemchen | 433/9 |
| 5,971,754 | A * | 10/1999 | Sondhi et al. | 433/24 |
| 6,123,544 | A | 9/2000 | Cleary | |
| 6,183,249 | B1 * | 2/2001 | Brennan et al. | 433/9 |
| 6,322,360 | B1 * | 11/2001 | Burgio | 433/80 |
| 6,554,612 | B2 | 4/2003 | Georgakis et al. | |
| 6,582,226 | B2 | 6/2003 | Jordan et al. | |
| 6,960,079 | B2 * | 11/2005 | Brennan et al. | 433/9 |
| 7,020,963 | B2 | 4/2006 | Cleary et al. | |
| 2003/0198915 | A1 * | 10/2003 | White | 433/21 |
| 2004/0054304 | A1 | 3/2004 | Raby | |
| 2004/0219473 | A1 * | 11/2004 | Cleary et al. | 433/9 |
| 2005/0074716 | A1 | 4/2005 | Cleary et al. | |
| 2005/0133384 | A1 | 6/2005 | Cinader et al. | |
| 2006/0084026 | A1 * | 4/2006 | Cinader et al. | 433/24 |
| 2006/0223021 | A1 * | 10/2006 | Cinader et al. | 433/3 |
| 2006/0223031 | A1 | 10/2006 | Cinader, Jr. et al. | |

FOREIGN PATENT DOCUMENTS

| WO | WO 02/089693 | 11/2002 |
|---|---|---|
| WO | WO 2004/014250 | 2/2004 |

* cited by examiner

*Primary Examiner*—Ralph A Lewis
*Assistant Examiner*—Sunil K Singh
(74) *Attorney, Agent, or Firm*—James D. Christoff (57) ABSTRACT

An orthodontic assembly includes an appliance placement device such as an indirect bonding transfer tray or a jig. A number of orthodontic appliances such as brackets are releasably connected to the placement device. The assembly also includes a dispensing unit that is adapted to receive the placement device and apply a quantity of adhesive to the bases of the appliances simultaneously.

13 Claims, 3 Drawing Sheets

ORTHODONTIC ADHESIVE DISPENSING ASSEMBLY

BACKGROUND OF THE INVENTION

1. Field of the Invention

This invention broadly relates to apparatus and methods for applying orthodontic adhesive to orthodontic appliances that are bonded to the patient's teeth. More particularly, the present invention relates to apparatus and methods for applying orthodontic adhesive to appliances used in indirect bonding procedures, such as appliances connected to indirect bonding trays or jigs.

2. Description of the Related Art

Orthodontic treatment involves movement of malpositioned teeth to desired locations in the oral cavity. Orthodontic treatment can improve the patient's facial appearance, especially in instances where the teeth are noticeably crooked or where the jaws are out of alignment with each other. Orthodontic treatment can also enhance the function of the teeth by providing better occlusion during mastication.

One common type of orthodontic treatment involves the use of tiny, slotted appliances known as brackets. The brackets are fixed to the patient's teeth and an archwire is placed in the slot of each bracket. The archwire forms a track to guide movement of teeth to desired locations.

The ends of orthodontic archwires are often connected to small appliances known as buccal tubes that are, in turn, secured to the patient's molar teeth. In many instances, a set of brackets, buccal tubes and an archwire is provided for each of the patient's upper and lower dental arches. The brackets, buccal tubes and archwires are commonly referred to collectively as "braces".

In many types of orthodontic techniques, the precise position of the appliances on the teeth is an important factor for helping to ensure that the teeth move to their intended final positions. For example, one common type of orthodontic treatment technique is known as the "straight-wire" technique, where the archwire lies in a horizontal plane at the conclusion of treatment. Consequently, if a bracket is attached to the tooth at a location that is too close to the occlusal or outer tip of the tooth, the orthodontist using a straight-wire technique will likely find that the tooth in its final position is unduly intruded. On the other hand, if the bracket is attached to the tooth at a location closer to the gingiva than is appropriate, it is likely that the final position of the tooth will be more extruded than desired.

In general, orthodontic appliances that are adapted to be adhesively bonded to the patient's teeth are placed and connected to the teeth by either one of two techniques: a direct bonding technique, or an indirect bonding technique. In the direct bonding technique, the appliance and adhesive are grasped with a pair of tweezers or other hand instrument and placed by the practitioner on the surface of the tooth in an approximate desired location. Next, the appliance is shifted along the surface of the tooth as needed until the practitioner is satisfied with its position. Once the appliance is in its precise, intended location, the appliance is pressed firmly onto the tooth to seat the appliance in the adhesive. Excess adhesive in areas adjacent the base of the appliance is removed, and the adhesive is then allowed to cure and fix the appliance firmly in place.

While the direct bonding technique described above is in widespread use and is considered satisfactory by many, there are shortcomings that are inherent with this technique. For example, access to surfaces of malposed teeth may be difficult. In some instances, and particularly in connection with posterior teeth, the practitioner may have difficulty seeing the precise position of the bracket relative to the tooth surface. Additionally, the appliance may be unintentionally dislodged from its intended location during the time that the excess adhesive is being removed adjacent the base of the appliance.

Another problem associated with the direct bonding technique described above concerns the significant length of time needed to carry out the procedure of bonding each appliance to each individual tooth. Typically, the practitioner will attempt to ensure that each appliance is positioned in its precise, intended location before the adhesive is cured, and some amount of time may be necessary before the practitioner is satisfied with the location of each appliance. At the same time, however, the patient may experience discomfort during the procedure and have difficulty in remaining relatively motionless, especially if the patient is an adolescent. As can be appreciated, there are aspects of the direct bonding technique that can be considered a nuisance for both the practitioner and for the patient.

Indirect bonding techniques avoid many of the problems noted above. In general, indirect bonding techniques known in the past have involved the use of a placement device having a shape that matches the configuration of at least part of the patient's dental arch. One type of placement device is often called a "transfer tray" and typically has a cavity for receiving a number of teeth simultaneously. A set of appliances such as brackets are releasably connected to the tray at certain, predetermined locations.

Other types of placement devices used in indirect bonding are often referred to as "jigs" and resemble a framework that contacts one or more teeth at certain locations. For example, a jig constructed for use in bonding a single appliance to a single tooth may have an arm that extends over and contacts an incisal section of the tooth. An appliance such as a bracket is releasably connected to the jig at a certain, predetermined location relative to the tooth.

During the use of orthodontic placement devices for indirect bonding, an adhesive is typically applied to the base of each appliance by the orthodontist or a staff member. The placement device is then placed over the patient's teeth and remains in place until such time as the adhesive hardens. Next, the placement device is detached from the teeth as well as from the appliances, with the result that all of the appliances previously connected to the placement device are now bonded to respective teeth at their intended, predetermined locations.

Indirect bonding techniques offer a number of advantages over direct bonding techniques. For one thing, and as indicated above, it is possible to bond a plurality of appliances to a patient's dental arch simultaneously, thereby avoiding the need to bond each appliance in individual fashion. In addition, the placement device helps to locate the appliances in their proper, intended positions such that adjustment of each appliance on the surface of the tooth before bonding is avoided. The increased placement accuracy of the appliances that is often afforded by indirect bonding techniques helps ensure that the patient's teeth are moved to their proper, intended positions at the conclusion of treatment.

In recent years, many improvements have been made in the field of indirect bonding. For example, U.S. Pat. No. 5,971,754 (Sondhi et al.) describes a two-component indirect bonding adhesive with a relatively fast curing time that reduces the length of time that the tray must be firmly held against the patient's teeth. U.S. Pat. No. 6,123,544 (Cleary) describes a transfer tray that receives movable arms for placing appliances on the patient's teeth once the tray is positioned in the oral cavity. U.S. Pat. No. 7,020,963 (Cleary et al.) describes among other things a transfer apparatus with an improved matrix material for releasably holding appliances in place. Published U.S. Patent Application No. 2005/0074716-A1 (Cleary et al.) describes a placement device with appliances that are precoated by the manufacturer and received in a container for convenient use by the practitioner when desired.

A wide variety of orthodontic adhesives are available, and some practitioners prefer to use orthodontic adhesives with relatively low viscosities. However, low viscosity adhesives pose difficulties when precoated onto the base of appliances by the manufacturer. For example, the adhesive may not be sufficiently stiff to enable the adhesive to retain its shape and stay in its proper place on the base of the appliances during shipping and handling of the container and until such time as the container has been opened by the practitioner.

In addition, there is a continuing need to improve the state of the art of indirect bonding so that the practitioner's time in completing the bonding procedure is reduced. Such a reduction in time may also serve to benefit the patient since the amount of chair time is reduced as well.

SUMMARY OF THE INVENTION

The present invention is directed toward an orthodontic appliance placement device and adhesive dispensing assembly. The placement device, such as a transfer tray or jig, includes a plurality of orthodontic appliances. An adhesive dispensing unit is constructed to receive the placement device and apply a quantity of orthodontic adhesive to the base of a number of appliances simultaneously.

In more detail, the present invention in one aspect is directed to an orthodontic assembly that comprises an orthodontic appliance placement device having wall sections that match the configuration of at least a portion of a patient's dental arch. The assembly also includes a number of orthodontic appliances that are releasably connected to the placement device. Each of the appliances has a base for bonding the appliance to a tooth. The assembly further includes an adhesive dispensing unit having wall portions adapted to matingly receive the placement device. The dispensing unit has a plurality of adhesive applicators, and each applicator is positioned to apply a quantity of orthodontic adhesive on the base of one of the appliances when the placement device is received on the dispensing unit.

Another aspect of the present invention is also directed toward an orthodontic assembly. In this aspect, the assembly comprises an indirect bonding transfer tray having wall sections that match the configuration of at least a portion of a patient's dental arch. In addition, the assembly includes a number of orthodontic appliances that are releasably connected to the wall sections. Each of the appliances has a base for bonding the appliance to a tooth. The assembly also includes a model dental arch having a configuration similar to at least a portion of the patient's dental arch. The model dental arch includes a number of model teeth. The assembly additionally includes a quantity of orthodontic adhesive that extends over at least a portion of some of the model teeth. Each quantity of orthodontic adhesive is positioned relative to the model teeth to contact the base of one of the appliances when the transfer tray is placed on the model dental arch.

These and other aspect of invention will be described in more detail below and are illustrated in the accompanying drawings.

DEFINITIONS

"Mesial" means in a direction toward the center of the patient's curved dental arch.

"Distal" means in a direction away from the center of the patient's curved dental arch.

"Occlusal" means in a direction toward the outer tips of the patient's teeth.

"Gingival" means in a direction toward the patient's gums or gingiva.

"Facial" means in a direction toward the patient's cheeks or lips.

"Lingual" means in a direction toward the patient's tongue.

DETAILED DESCRIPTION OF THE PREFERRED EMBODIMENTS

An orthodontic assembly according to one embodiment of the invention is illustrated in FIGS. 1-4 and is designated by the numeral 10. The orthodontic assembly 10 broadly includes a placement device or transfer tray 12 (also shown in FIG. 5) and a number of orthodontic appliances 14 that are releasably connected to the transfer tray 12. The assembly 10 also includes an adhesive dispensing unit 16 that releasably receives the transfer tray 12 when desired to apply adhesive to the appliances 14.

In more detail, the transfer tray 12 includes a channel 18 (see, e.g., FIGS. 3 and 5) having a shape that matches a negative image of one of the patient's dental arches. In the exemplary tray 12 shown in the drawings, the channel 18 is adapted to matingly receive a patient's lower dental arch, although it should be understood in this regard that as an alternative the transfer tray 12 may have a shape adapted to receive the patient's upper dental arch.

The tray 12 may be constructed according to any one of a variety of known techniques. In the example shown in FIGS. 1-5, the tray 12 includes an outer shell 20 that is relatively stiff and an inner section of matrix material 22 that is relatively flexible. A suitable material for the shell 20 is a sheet of polycarbonate such as Makrolon brand material from Bayer or Lexan brand polycarbonate from GE having a thickness of 0.06 in. (1.5 mm). Other materials, such as polyethyleneterephthalate ("PET"), polyethyleneterephthalate glycol ("PETG") or polystyrene may also be used.

Preferably, the matrix material 22 has a relatively low viscosity before hardening so that intimate contact between the matrix material 22 and orthodontic appliances received in the channel 18 is assured. In this manner, the matrix material 22 is able to substantially penetrate in various recesses, cavities and other structural features of each appliance so that a secure connection between the appliance and the matrix material 22 can be established. An example of a suitable matrix material having a relatively low viscosity before curing is a silicone material such as "RTV615" silicone material from General Electric.

The matrix material 22 preferably has a viscosity before curing that is less than about 60,000 cp. More preferably, the matrix material 22 has a viscosity before curing that is less than about 25,000 cp. Most preferably, the matrix material has a viscosity that is less than about 8,000 cp. Once hardened, the matrix material 22 has a Shore A hardness that is in the range of about 10 to about 80, more preferably in the range of about 30 to about 60 and most preferably in the range of about 40 to about 50.

Alternatively, the matrix material 22 may comprise a dental impression material or a bite registration material. Suitable materials include polyvinylsiloxane impression material, such as Memosil 2 brand vinyl polysiloxane material from Heraeus Kulzer Inc., or Peppermint Snap brand clear bite registration material from Discus Dental. Another suitable matrix material is Affinity Crystal brand silicone impression material from Clinician's Choice Dental Products, Inc. If a light-curable adhesive is to be subsequently used for bonding the appliances to the patient's teeth, the matrix material 22 is preferably optically clear and transmits actinic radiation without substantial absorption once hardened.

Preferably, the inner wall sections of the matrix material 22 that face the channel 18 have contours that precisely match the contours of the individual teeth of the patient, as well as an overall configuration that matches the orientation of each tooth relative to other teeth in the same dental arch when the teeth are in their initial malocculed condition at the beginning of treatment. As a result, when the tray 12 is placed over the patient's dental arch, the channel 18 of the tray 12 provides a mating fit with the patient's teeth such that little, if any, tolerance or "slop" is present and relative movement between the tray 12 and the dental arch is substantially hindered.

The orthodontic appliances 14 are detachably connected to the matrix material 22 of the tray 12. In FIGS. 1-5, the exemplary illustrated orthodontic appliance 14 is an orthodontic bracket, although other appliances are also possible. Examples of other suitable appliances include buccal tubes, buttons, formed "bumps" made, e.g., of composite material, or any other metal or non-metal "handle" or other structure connected to the teeth that provides an attachment point for a force member such as a wire, aligner tray, polymeric strip, elastomeric band or chain, or any combination of the foregoing. If desired, the appliances may be omitted for some of the teeth in the dental arch such as molar teeth or teeth that have only partially erupted.

Figure 1:
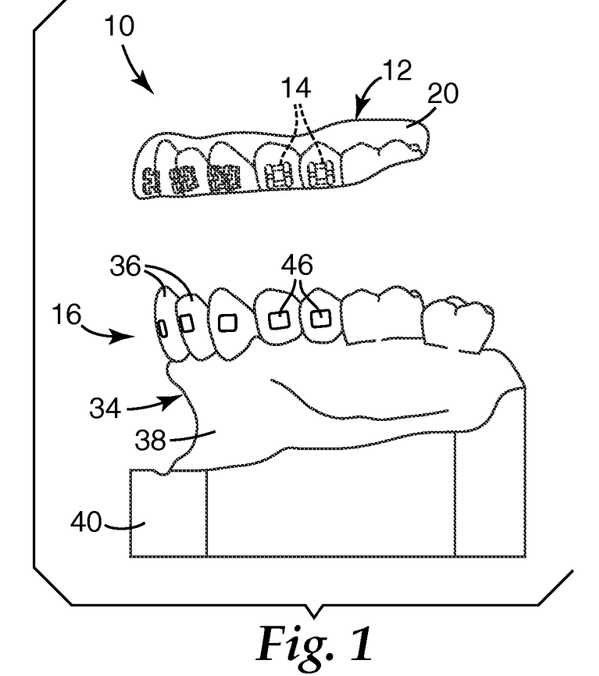
FIG. 1 is a side elevational view of an orthodontic assembly constructed in accordance with one embodiment of the present invention, showing a placement device of the assembly that is spaced apart from an adhesive dispensing unit of the assembly.
Figure 2:
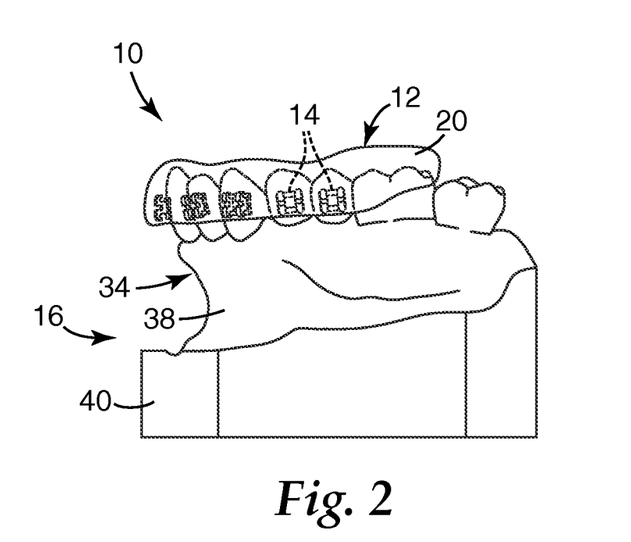
FIG. 2 is a view somewhat similar to FIG. 1 except that the placement device has been received on the adhesive dispensing unit.
Figure 3:
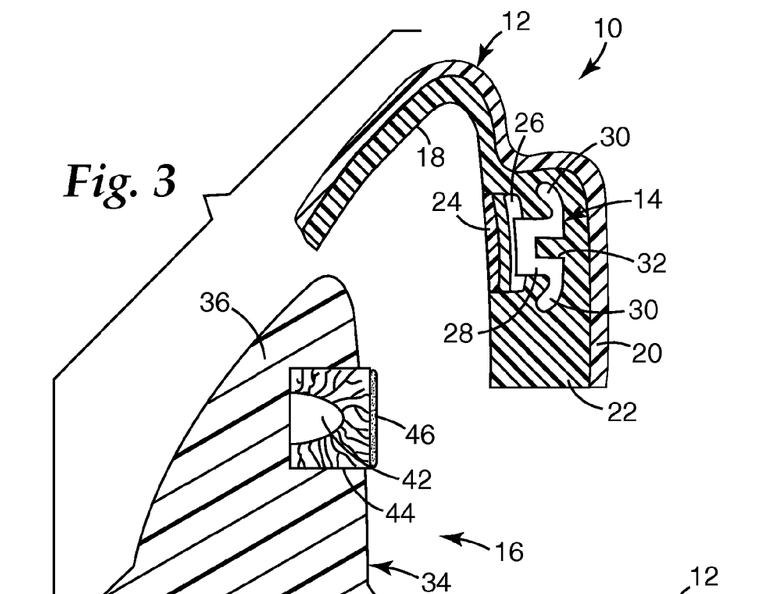
FIG. 3 is an enlarged cross-sectional view of the orthodontic assembly as shown in FIG. 1.
Figure 4:
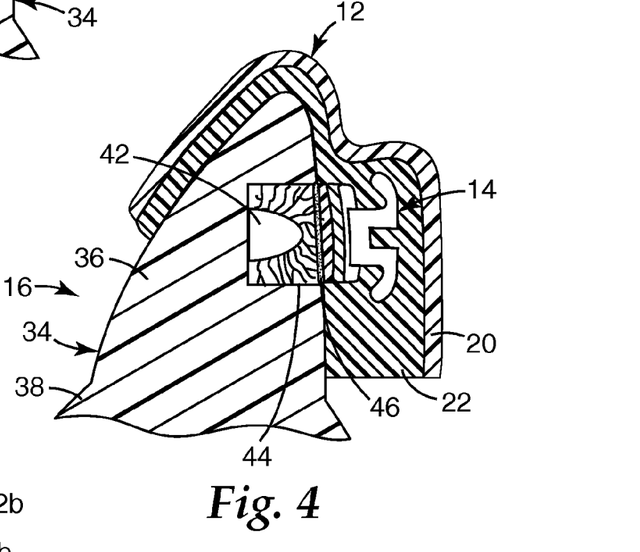
FIG. 4 is an enlarged cross-sectional view of the orthodontic assembly as it appears in FIG. 2.
Figure 5:
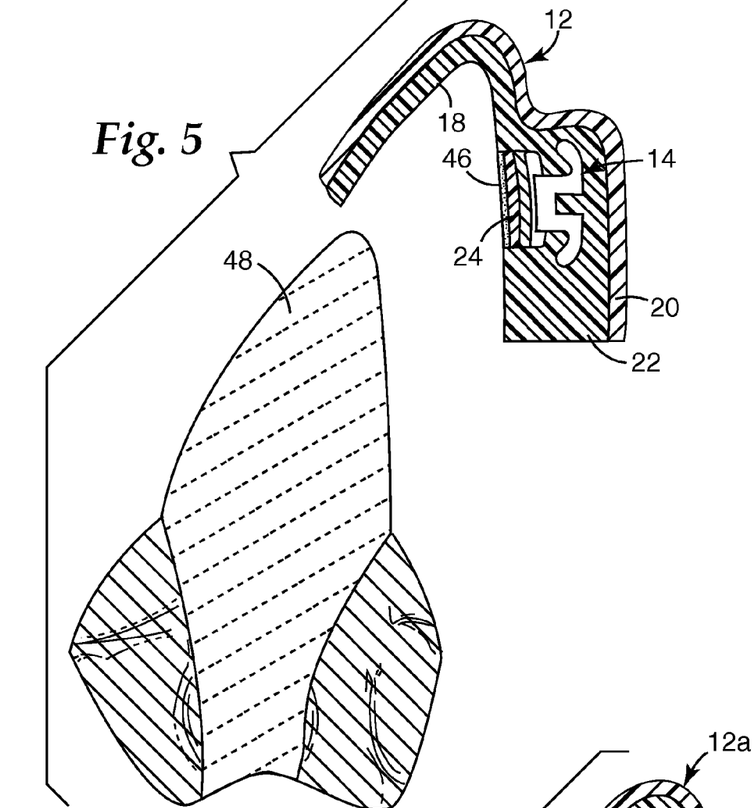
FIG. 5 is an enlarged cross-sectional view of the placement device shown in FIGS. 1-4, depicting the placement device as it might appear after a quantity of adhesive has been applied to the base of an orthodontic appliance, and also depicting one of the patient's teeth.

The exemplary appliance 14 as shown in FIGS. 1-5 includes a base 24 (see, e.g., FIG. 3) that is connected to a base flange 26. The appliance 14 also has a body 28 that extends outwardly from the base flange 26. Four tiewings 30 (only two are shown in FIGS. 3-5) are connected to the body 28, and an archwire slot 32 extends through a space between the tiewings 30.

The base flange 26, the body 28 and the tiewings 30 may be made of any one of a number of materials suitable for use in the oral cavity and having sufficient strength to withstand the correction forces applied during treatment. Suitable materials include, for example, metallic materials (such as stainless steel), ceramic materials (such as monocrystalline or polycrystalline alumina) and plastic materials (such as fiber-reinforced polycarbonate). Optionally, the base flange 26, the body 28 and the tiewings 30 are integrally made as a unitary component.

The base 24 of the appliance 14 is preferably made of a material different than the material comprising the base flange 26, and has a configuration that matches the configuration of a portion of a patient's tooth structure. More particularly, the base 24 has a concave contour that is a replica of the convex contour of the portion of the patient's tooth that represents the ultimate desired location of the appliance 14 on the tooth. Optionally, the concave contour of the base 24 is a compound concave contour (i.e., curved in directions along two mutually perpendicular reference planes).

Suitable methods for making the tray 12 and the base 24 are described in U.S. Pat. No. 7,020,963 (Cleary et al.), published U.S. patent application Ser. No. 20040219473 (Cleary et al.) and pending U.S. patent application Ser. No. 11/098317, entitled "METHOD OF MAKING INDIRECT BONDING APPARATUS FOR ORTHODONTIC THERAPY". Preferably, the tray 12 also includes occlusal stops such as described in pending U.S. patent application Ser. No. 11/098716 entitled "ORTHODONTIC INDIRECT BONDING APPARATUS WITH OCCLUSAL POSITIONING STOP MEMBERS". Other constructions for the tray 12 are also possible, such as the trays described in U.S. Pat. No. 5,971,754 (Sondhi et. al).

The dispensing unit 16 in this embodiment includes a model 34 of the patient's lower dental arch. The dental model 34 includes a number of model teeth 36, corresponding to each tooth of the patient's lower dental arch. The dental model 34 also optionally includes model gingival tissue 38 as well as a base or pedestal 40 (FIGS. 1 and 2).

Optionally, the model 34 is a replica of the model used by the manufacturer to make the transfer tray 12. As yet another option, the dental model 34 is the same model that is used earlier during the manufacturing process to make the transfer tray 12.

Optionally, the dental model 34 is made by first taking an impression of the patient's lower dental arch, using care to avoid undue distortion. An alginate impression material may be used, such as Unijel II brand alginate impression material from 3M Unitek. Alternatively, a hydrocolloid or vinyl polysiloxane impression material may be used, such as Position brand Penta brand vinyl polysiloxane impression material from 3M ESPE.

The dental model 34 is then made from the impression. Optionally, the dental model 34 is a "stone" model made from plaster of Paris, using care to avoid bubbles in the model. If small voids are present, the voids can be filled with a small, additional quantity of plaster of Paris. As an option, the dental model 34 includes only the model teeth 36 and sufficient model gingival tissue 38 to hold the model teeth 36 together.

As an alternative, the model 34 may be made using digital data that is representative of the patient's teeth and adjacent gingival tissue. The digital data may be obtained by use of a hand-held intra-oral scanner or other device known in the art. As another alternative, the digital data may be obtained by scanning an impression or a stone model. The model 34 may then be made from the digital data using, for example, a stereo lithographic printer.

The model 34 may also be made using digital data in conjunction with a milling process. For example, a CNC milling machine, similar to the CAD/CIM milling machines sold by Cerec Network of Buelach, Switzerland, may be used to mill replicas made of ceramic, composite or other materials. An intra-oral camera, similar to the cameras associated with the Cerec machines, may be used to obtain digital data representing the shape of the dental arches. Alternatively, a scanner may be used to scan an impression or a model of an impression to obtain the digital data.

If the orthodontic practitioner takes the impression, the practitioner could send either the impression or the replica to a manufacturer of indirect bonding trays. Alternatively, the practitioner could send a digital data file of scanned teeth. In either instance, the practitioner preferably also sends his or her instructions regarding placement of the appliance on the teeth.

Preferably, the model 34 is an accurate representation of the patient's oral structure. In particular, the model teeth 36 will have a configuration and orientation that is identical to the configuration and orientation of the corresponding teeth of the orthodontic patient. In addition, the model gingival tissue 38 will have a shape that matches the shape of the corresponding portions of the gingival tissue of the patient.

This dispensing unit 16 also includes a plurality of adhesive applicators 42, each of which is connected to a respective one of the model teeth 36. In this embodiment, each of the adhesive applicators 42 includes an array of small resilient fibers that are received in a recess 44 located in a front or labial portion of the surface of the model tooth 36. Preferably, the fibers protrude in a labial direction slightly past the adjacent portions of the model tooth surface.

An example of a suitable applicator 42 is the outer tip portion of a disposable applicator from Microbrush Corporation of Grafton, Wis. and commercialized under the brand name "Microbrush". The outer tip portion of this application includes fibers that extend outwardly in a generally radial direction. The tip portion bearing the fibers is severed from an elongated handle of the applicator and placed within the recess 44 of the model tooth 36. A small quantity of adhesive may be used to retain the tip portion in place.

Other examples of suitable applicators 42 include non-woven pads and sections of felt or cellulosic materials. The applicators 42 may also be constructed of foam materials, such as the foam materials described below in connection with applicators 42a.

A quantity of orthodontic adhesive 46 is retained by the applicator 42 as shown for example in FIG. 3. As used herein, adhesive 46 may be any orthodontic adhesive suitable for use as an indirect bonding adhesive, or any component of such an adhesive. Preferably, the adhesive 46 is a liquid and is initially retained on or within the applicator 42. For example, if the applicator 42 includes fibers, the adhesive 46 substantially saturates the fibers.

Suitable adhesives 46 include composites, compomers, glass ionomers and resin-modified glass ionomers. Examples of light-curable adhesives include Transbond brand XT primer, Transbond brand MIP primer and Transbond LR brand adhesive from 3M Unitek and Adper brand Single Bond, Adper brand Single Bond Plus and Adper brand Scotchbond brand adhesives from 3M ESPE. Examples of chemical curing adhesives include Sondhi brand adhesive, Concise brand adhesive and Multi-Cure brand glass ionomer cement from 3M Unitek. If adhesive 46 is one component of a two-component bonding adhesive, the other component may be applied by the practitioner to the patient's teeth immediately before the appliances are received on the patient's teeth.

Optionally, the adhesive 46 includes a color-changing property that facilitates the cleaning of flash (i.e., excess adhesive) along the periphery of the base 24 once the appliances 14 are in place. Examples of suitable color-changing adhesives are described in U.S. Pat. No. 6,960,079 (Brennan et al.). The adhesive 46 may include fluoride ions that release during the course of orthodontic treatment. Fluoride may be included in a compomer adhesive or in a glass ionomer adhesive. The release of fluoride in the patient's oral cavity helps reduce the formation of caries, and is especially beneficial for adolescent patients who are not rigorous in maintaining good oral hygiene in the vicinity of the appliances 14.

Particularly preferred liquid adhesives 46 include hydrophilic compositions, such as some of the liquid orthodontic primers that are commercially available. The liquid adhesive 46 may include one or more monomers, oligomers, polymers or copolymers or mixtures of the foregoing. The liquid adhesive 46 may also contain additives such as pigments and/or antioxidants. The liquid adhesive 46 optionally contains solid filler particles such as fumed or fused silica, fluoroaluminosilicate, quartz, zirconia, and the filler particles could optionally be coated for example with silane, zirconate or titanate coatings as dispersion aids. The liquid adhesive 46 may also include a fluoride releasing material such as zinc fluoride. As another option, the liquid adhesive 46 may include a material that serves to etch the tooth enamel when placed into contact with a tooth. Preferably, the liquid adhesive 46 includes hydrophilic monomers, oligomers, polymers or blends thereof that optionally have the ability to absorb moisture and also provide enhanced chemical bonding to tooth enamel.

Preferred moisture tolerant or hydrophilic materials for the liquid adhesive 46 include 2-hydroxyethyl acrylate, 2-hydroxyethyl methacrylate ("HEMA"), hydroxypropyl acrylate, hydroxypropyl methacrylate, glycerol di-acrylate, glycerol di-methacrylate, polyethylene glycol mono methacrylate, polypropylene glycol mono methacrylate, tetrahydrofurfuryl acrylate, tetrahydrofurfuryl methacrylate, glycidyl acrylate, glycidyl methacrylate and the like. Other preferred hydrophilic monomers include glycerol mono- and di-acrylate, glycerol mono- and di-methacrylate, ethyleneglycol diacrylate, ethyleneglycol dimethacrylate, polyethyleneglycol diacrylate (where the number of repeating ethylene oxide units vary from 2 to 30), polyethyleneglycol dimethacrylate [where the number of repeating ethylene oxide units vary from 2 to 30, especially triethylene glycol dimethacrylate ("TEGDMA").

More specific examples of hydrophilic materials are non-ionic polymers or copolymers, e.g. polyalkylene oxides (polyoxymethylene, polyethyleneoxide, polypropylene oxide) polyethers (polyvinylmethyl ether), polyethyleneimine copolymers, polyacrylamides and polymethacrylamides, polyvinylalcohol, saponified polyvinylacetate, polyvinylpyrrolidone, polyvinyloxazolidone, polymers containing N-oxysuccinimdo groups, ionic or ionizable polymers and copolymers containing polyacrylic acid, polymethacrylic acid in unionized, partially neutralized or fully neutralized form, polyethyleneimine and its salts, polyethylene sulfonic acid and polyaryl sulfonic acids in unionized, partially neutralized or fully neutralized form, polyphosphoric and polyphosphonic acids in unionized, partially neutralized or fully neutralized form.

Preferred hydrophilic materials may be prepared by reaction of vinylic monomers such as acrylates, methacrylates, crotonates, itaconates and the like that contain polar groups that are acidic, basic or provided as a salt. These groups can also be ionic or neutral.

Examples of polar or polarizable groups include neutral groups such as hydroxy, thio, substituted and unsubstituted amido, cyclic ethers (such as oxanes, oxetanes, furans and pyrans), basic groups (such as phosphines and amines, including primary, secondary, tertiary amines), acidic groups (such as oxy acids, and thiooxyacids of C, S, P, B) and ionic groups (such as quarternary ammonium, carboxylate salt, sulfonic acid salt and the like) and the precursors and protected forms of these groups.

In FIG. 3, the transfer tray 12 is illustrated as it might appear immediately before it is received on the dental model 34. In FIG. 4, the transfer tray 12 has been received on the dental model 34. When the transfer tray 12 is received on the dental model 34, the base 24 of each appliance 14 is located directly in front (i.e., in a labial direction) of a corresponding applicator 42 and as a result the base 24 contacts the adhesive 46 that has been previously received by the applicators 42.

Next, the transfer tray 12 is detached from the dental model 34. As the appliances 14 are moved away from the respective model teeth 36, the corresponding quantity of adhesive 46 releases from the applicator 42 and remains in engagement with the base 24. FIG. 5 illustrates the transfer tray 12 and the appliances 14, where the adhesive 46 has been transferred to the base 24 of each appliance 14. The transfer tray 12 as depicted in FIG. 5 is now ready for use in an indirect bonding procedure.

The steps of the indirect bonding procedure are determined in part by the particular adhesive 46 that is selected by the practitioner. For example, if Transbond brand Plus Self Etching primer from 3M Unitek is selected, the patient's teeth that are to receive the appliances 14 are isolated using cheek retractors, tongue guards, cotton rolls, dry angles and/or other articles as needed. Excess water from the teeth is then removed using pressurized air from an air syringe. After the primer is mixed following the manufacturer's directions, the primer is rubbed onto the teeth for three to five seconds in the general area that is to be covered by the appliances 14, taking care to prevent the etching solution from flowing into interproximal contacts or engaging the skin or gingiva.

After the primer has been applied to all of the teeth of the dental arch, a three-second gentle airburst is directed to each tooth to dry the primer into a thin film.

Preferably, the tooth preparation steps as mentioned above are carried out before the adhesive 46 is transferred to the base 24 of the appliances 14 as shown in FIG. 4. In this manner, the adhesive 46 is not unduly exposed to ambient light, air or contaminates and the tray 12 may be immediately placed over the patient's dental arch as soon as the tray 12 is disengaged from the dental model 34.

The shell 20 is then positioned over the corresponding teeth and seated, optionally with a swinging, hinge-type motion. In FIG. 5, an exemplary tooth of the patient is designated by the numeral 48. Since the shape of the channel 18 of the matrix material 22 matches the shape of the underlying teeth 48, the appliances 14 are simultaneously seated against the underlying teeth 48 at precise locations corresponding to previous locations selected by the practitioner. Preferably, pressure is then applied to the occlusal, labial and buccal surfaces of the shell 20 until such time as the adhesive 46 has sufficiently hardened. Optionally, finger pressure may be used to firmly press the appliances 14 against the enamel surfaces of the patient's teeth 48.

Once the adhesive 46 has hardened, the shell 20 is carefully removed from the patient's dental arch. Preferably, the shell 20 is first separated from the matrix material 22, which remains in place over the dental arch along with the appliances 14. Next, the matrix material 22 is detached from the appliances 14. A hand instrument such as a scaler may be used to help hold each appliance 14 against the surface of the respective tooth 48 of the patient as the matrix material 22 is peeled away from the appliances 14. However, in instances where a relatively soft matrix material is employed or otherwise readily releases from the appliances 14, the use of a scaler to help avoid fracturing the fresh adhesive bond is optional.

As another option, the shell 20 may be separated from the matrix material 22 before the adhesive 46 has hardened. This option is particularly useful when the adhesive 46 is a light-curable adhesive.

After the matrix material 22 has been detached from the appliances 14, an archwire is placed in the slots of the appliances 14 and ligated in place. Suitable ligation devices include tiny, elastic O-rings as well as sections of wire that are tied in a loop around the appliances 14. As another option, the appliances 14 may be self-ligating appliances that include a latch for releasably engaging the archwire such as those described in U.S. Pat. No. 6,582,226 (Jordan et al.) and U.S. Pat. No. 6,554,612 (Georgakis et al.) and PCT Publication No. WO02/089693 (Georgakis et al.).

Preferably, the location of the applicators 42 on the model teeth 36 is selected to correspond to the locations of the appliances 14 once the appliances 14 are received on the patient's teeth 48. As one technique, hand instruments such as gauges may be used to determine the location of the applicators 42 on the model teeth 36 so that the recesses 44 are provided in a proper location. For instance, if the archwire slot of a particular appliance 14 is to be 5 mm from the incisal edge of the patient's tooth, a 5 mm gauge may be used to assist in drawing a pencil line on the model tooth 36 that is 5 mm from its incisal edge. Next, the intersection of the long axis of the model tooth 36 is marked along a drawn pencil line, using a visual assessment of the shape of the model tooth 36 to determine the location of the long axis. The intersection identifies the center of the location for the recess 44.

As another option, computer software may be used to determine the proper placement of the selected appliance 14 and hence the proper location of the recess 44 for the applicator 42. As one example, the practitioner may desire the appliance 14 to be aligned with the facial axis point of the clinical crown (the "FA point") of the tooth, such that the archwire slot of the appliance 14 is oriented in a plane parallel to the patient's occlusal plane and the occlusal-gingival axis of the appliance 14 is aligned with the long axis of the patient's tooth 48. The software utilizes a digital data file representative of the patient's tooth 48 and determines the location of the FA point. The FA point on the model tooth 36, corresponding to the same FA point on the patient's tooth 48, is then located. In addition, the orientation of the archwire slot 32 and the occlusal-gingival axis of the appliance 14 are then determined with respect to the model tooth 36, using the FA point of the model tooth 36, a determination of the occlusal plane of the dental arch and a determination of the long axis of the model tooth 36. A suitable computer program for determining the long axis of a tooth is described in U.S. Patent Publication No. 2004/0054304 (Raby).

In instances where the dental model 34 is made by a stereolithography process, the recesses 44 may be formed at the same time that the dental model 34 is made. Alternatively, in instances where the dental model 34 is also used to make the transfer tray 12, the recesses 44 are formed after the tray 12 is made. In addition, the shape of the applicators 42 preferably corresponds to the overall shape of the base 24 of the corresponding appliance 14. Such construction helps ensure that the adhesive 46 is transferred only to the base 24 of the appliances 14 and not to adjacent wall surfaces of the transfer tray 12 that face the channel 18.

The dispensing unit 16 is advantageous, in that the bases 24 of a number of appliances 14 are simultaneously coated with a quantity of adhesive 46. As a result, the application of adhesive 46 to the base 24 of each appliance 14 in individual, seriatim fashion is avoided. Moreover, the quantity of adhesive 46 that is received on each of the applicators 42 can be precisely measured in advance by a manufacturer using automated dispensing equipment in order to help ensure that a proper quantity of adhesive 46 is transferred to the base 24 of each appliance 14. As one example, an air-activated syringe dispensing unit, connected to the end of a robotic arm, maybe used by the manufacturer to dispense adhesive 46 onto the applicators 42.

As an additional option, the quantity of adhesive 46 that is applied to each applicator 42 may vary in accordance with the type of appliance 14 and/or with the overall size of the base 24 of the appliance 14. Furthermore, the characteristics of the adhesive 46 may vary from applicator 42 to the next. For example, the adhesive 46 may vary by viscosity, tack, bond strength, hydrophilicity, color-changing ability, composition and/or curing mechanism in accordance with the type of appliance 14 or location of the tooth 48 in the dental arch. Examples of options for varying the characteristics of the adhesive 46 from applicator 42 to applicator 42 are described in U.S. Patent Publication No. 2005/0133384 (Cinader et al).

The assembly 10 is particularly advantageous for use in the practitioner's office in instances where the adhesive 46 has a relatively low viscosity. In that instance, the transfer tray 12 is placed on the dental model 34 to transfer the adhesive 46 to the appliances 14 immediately before use. As such, there is less likelihood that the adhesive 46 will slide downward under the influence of gravity across the base 24 of the appliances 14 and detach from the appliance 14 before such time as the base 24 is placed over the patient's tooth. Preferably, the transfer tray 12 and the dispensing unit 16 are shipped to the practitioner's office simultaneously and preferably in different compartments of the same container.

The transfer tray 12 as illustrated in FIGS. 1-5 is constructed to extend substantially along the entire dental arch of the patient. As an alternative, however, the transfer tray 12 may be shorter in length and carry a correspondingly smaller number of appliances 14. For example, the transfer tray 12 may be constructed to fit over only one quadrant of the patient's dental arch, and include only those appliances 14 for some or all of the teeth of that quadrant.

Figure 6:
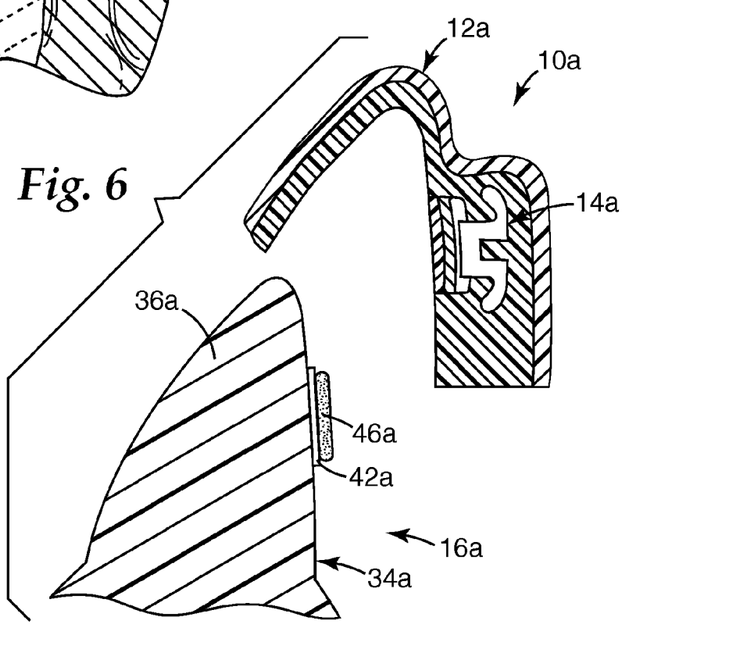
FIG. 6 is a cross-sectional view somewhat similar to FIG. 3 except showing an orthodontic assembly that is constructed in accordance with another embodiment of the invention.

An orthodontic assembly 10a according to another embodiment of the invention is illustrated in FIG. 6. The assembly 10a includes a transfer tray 12a and a number of appliances 14a that are detachably connected to the transfer tray 12a. The assembly 10a also includes a dispensing unit 16a that releasably receives the transfer tray 12a for applying adhesive 46a to the appliances 14a when desired.

The dispensing unit 16a includes a dental model 34a having a plurality of model teeth 36a. A number of applicators 42a are connected to labial surfaces of the model teeth 36a, and a quantity of the adhesive 46a is initially received on each of the applicators 42a.

The applicators 42a function in a manner similar to the applicators 42, in that the applicators 42a serve to apply the adhesive 46a to the base of the appliances 14a when the transfer tray 12a is placed over the dental model 34a. However, in this embodiment, the applicators 42a comprise a flat, sheet-like section of a release surface that readily releases the adhesive 46a when desired for transfer to the appliances 14a. Preferably, each applicator 42a readily releases the adhesive 46a such that little if any of the adhesive 46a remains on the applicator 42a. Additionally, in instances where the adhesive 46a is a paste and not a liquid, the applicator 42a enables the adhesive 46a to detach without undue distortion of the overall shape of the adhesive 46a.

Examples of suitable release surfaces include polymeric foams having either an open cellular structure or a closed cellular structure. If the release surface comprises foam, the foam is preferably a closed cell foam, is preferably compressible and is preferably resilient.

Preferably, the outwardly facing, labial side of the foam release surface has pores with a diameter that are mostly, if not entirely, within the range of about 0.00005 inch (0.001 mm) to about 0.03 inch (0.8 mm). More preferably, the diameter of the pores is mostly, if not entirely, within the range of about 0.001 inch (0.02 mm) to about 0.01 inch (0.2 mm). An example of a suitable average pore size is 0.004 inch (0.1 mm) in diameter or alternatively in the range of about 0.006 inch (0.15 mm) to about 0.01 inch (0.2 mm). The pore size is determined by determining its diameter in a reference plane parallel to the plane of the upper face. If the pore does not present a circular shape in that reference plane, the pore size is determined by calculating the diameter of a circle presenting an area that is equal to the area of the pore in such reference plane.

Particularly preferred foam materials for the release surface of the applicator 42a include polyolefin foams such as polyethylene foams, polybutylene foams and polypropylene foams, or blends of the foregoing. Polyvinyl chloride foams, polyurethane foams and foam copolymers may also be employed. Examples of suitable polyethylene foams include L series, M series, S series and T series Minicel brand foams (such as series M200, M300 and T300) from Voltek. Another suitable foam is Volara brand 9EO skived foam from Voltek. Optionally, an outer layer of cells of the foam may be heated to "seal" or shrink the size of the pores by reducing the pore diameter and/or by reducing the pore depth in directions perpendicular to the plane of the upper face.

If the selected foam is shown to absorb one or more of the fluid components of the adhesive 46a over time, then the foam could be modified in some manner provided the release characteristics of the foam are not unduly impaired. For example, the labial side of the release surface could be fused or coated with an organic or inorganic barrier material to partially close some or all of the pores. Optionally, the barrier material is a curable monomeric system that is cured or partially cured to establish a crosslinked barrier, either at the upper face, in the body of the foam material, or both. As another option, the foam is coated or partially coated (and possibly immersed) in a liquid component that reduces the driving force for absorption.

When the release surface is made of a material other than a foam as described above, the optional pores mentioned above may be made using any other suitable process or structure. For example, a number of particles such as spherical or irregularly-shaped beads, shards or particles made of glass, ceramic, metal or other materials may be fixed to a backing layer of the release surface to provide pores. As another alternative, the upper face may have ridges, projections or other structure, either random or repeating, to provide a number of small pores. The pores may be made using a microreplication technique, such as the methods disclosed in U.S. Pat. No. 5,152,917 (Pieper et al.) and U.S. Pat. No. 5,500,273 (Holmes et al.).

The release surface of the applicator 42a may alternatively be made of other materials as well. For example, if the adhesive 46a is a paste, the release surface may be made of other polymers, copolymers or blends of polymers and copolymers such as polyesters, polyolefins, polyurethanes, fluoropolymers, (meth)acrylic, silicones, epoxies, synthetic rubbers, polycarbonates or vinyls. If the adhesive 46a is a liquid, release surface may also be made of non-woven materials, cellulosic materials, ceramic, glass or metal.

If the adhesive 46a is a paste, the release surface optionally includes a quantity of a liquid composition that extends across the upper face and is in contact with the adhesive 46a. The liquid composition may be either a contiguous layer of liquid or a non-contiguous layer, such a patterned or printed coating or a coating randomly applied. The liquid composition may be made of any liquid material that facilitates release of the adhesive 46a from the release surface when desired, and if curable may be uncured, partially cured or entirely cured when present on the dispensing unit 16a.

Preferably, if the optional liquid composition is used, the liquid composition is at least partially removed from the release substrate when the adhesive 46a detaches from the release surface, and remains with the adhesive 46a during bonding of the appliance 14a to the patient's tooth.

Preferably, the liquid composition enhances the properties of the adhesive 46a. For example, the liquid composition transferred to the adhesive 46a may increase the tackiness of the adhesive 46a, may increase the wettability of the adhesive 46a and/or may increase the moisture tolerant characteristics of the adhesive 46a. These enhanced properties may facilitate bonding of the appliance 14a and also decrease the likelihood of spontaneous debonding of the appliance 14a during the course of orthodontic treatment. Preferred liquid compositions include hydrophilic compositions, such as some of the liquid orthodontic primers that are commercially available and described above in detail. Preferably, the liquid composition "cures into" the adhesive 46a as the adhesive hardens, i.e., the liquid composition polymerizes with the adhesive. Optionally, the liquid composition is wholly or partially crosslinked into the adhesive as the adhesive hardens. Furthermore, the liquid composition is preferably immiscible with the adhesive over an extended period of time, so that the liquid composition does not unduly mix with the adhesive before the adhesive cures.

Additional information regarding the release surface of the applicators 42a, including other alternative constructions and materials, may be found in U.S. Pat. No. 6,183,249 (Brennan et al.). Optionally, the release surface of the applicator 42a may comprise part of the model tooth 36a, or be a coating that is applied to the model tooth 36a.

Other aspects of the assembly 10a are essentially the same as corresponding aspects of the assembly 10. Consequently a detailed description of such similar aspects need not be repeated.

Figure 7:
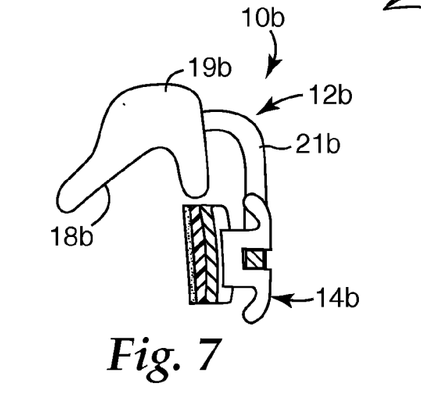
FIG. 7 is a cross-sectional view of a placement device of an orthodontic assembly that is constructed in accordance with yet another embodiment of the invention.

An orthodontic assembly 10b according to another embodiment of the invention is illustrated in FIG. 7. The orthodontic assembly 10b includes a placement device or jig 12b as well as a dispensing unit. The dispensing unit is not shown in the drawings but is preferably identical or similar to the dispensing units 16, 16a described above.

The jig 12b functions in a manner similar to the transfer tray 12, 12a, in that it includes a channel 18b with a configuration that matches a portion of the patient's dental arch. The jig 12b includes a body 19b that defines the channel 18b. Preferably, the body 19b is made of a soft material such as cured silicone impression material. Examples of suitable impression materials include "Express STD" brand impression material from 3M ESPE and other polyvinylsiloxane impression materials commercially available. The "RTV 615" brand silicone material from General Electric may also be employed.

The jig 12b also includes a series of arms 21b, each having a generally "L"-shaped configuration. One side of each arm 21b is embedded in the body 19b and the other side of the arm 21b is releasably connected to an orthodontic appliance 14b. Optionally, the arms 21b are made of an inexpensive plastic material such as polycarbonate.

The releasable connection between the arm 21b and the appliance 14b may comprise any suitable coupling means in accordance with the configuration or type of appliance 14b. In the example shown, the arm 21b extends along a vertical channel between spaced apart tiewings of the appliance 14b. The arm 21b is constructed so that the appliance 14b remains coupled to the arm 21b by friction until the bonding procedure has been completed and the adhesive has hardened.

Other types of releasable couplings are also possible. For example, the arm 21b may include an elastomeric member that snuggly extends around tiewings of the appliance 14b, and remains engaged with the appliance 14b until such time as the bonding procedure is complete. As another option, an adhesive is provided to detachably couple the arm 21b to the appliance 14b.

In use of the placement device or jig 12b, the adhesive is transferred by the dispensing unit to the base of the appliances 14b and the body 19b is then placed over the occlusal sections of the teeth of the selected dental arch. The arms 21b are constructed to engage the teeth at the proper pre-selected bonding locations as soon as the body 19b is seated in place. However, if desired, finger pressure may be applied to the arms 21b in order to ensure that the base of the appliances 14b is in close contact with the enamel surface of the patient's teeth.

Once the orthodontic bonding adhesive has hardened, the jig 12b is removed from the patient's oral cavity by disengaging the body 19b from the occlusal sections of the patient's teeth. At that time, the arms 21b detach from their respective appliances 14b, such that the latter remain in place firmly bonded to the patient's teeth.

A number of other variations, modifications and additions are also possible without departing from the spirit of the invention. For example, the applicators described above may be movable with respect to the model teeth, so that each applicator can be moved in a direction toward the base of the corresponding appliances once the placement device has been received on the model arch. As yet another option, the dispensing unit need not include a model dental arch, but instead comprise structure that receives the placement device in mating relation with applicators located in proper spatial relationship to apply adhesive to corresponding appliances.

All of the patents and patent applications mentioned above are hereby incorporated by reference. Moreover, the foregoing description is intended to exemplify various aspects of the invention and other variations are possible. Consequently, the invention should not be deemed limited to the presently preferred embodiments described above, but instead only by a fair scope of the claims that follow and their equivalents.

The invention claimed is:

1. A method of bonding orthodontic appliances to a patient's teeth comprising:
   providing an orthodontic appliance placement device having wall sections that match the configuration of at least a portion of the patient's dental arch;
   releasably connecting a number of orthodontic appliances to the placement device, wherein each of the appliances includes a base for bonding the appliance to a tooth;

providing an adhesive dispensing unit having wall sections matching portions of the patient's dental arch, wherein the adhesive dispensing unit includes a plurality of adhesive applicators each including a quantity of unhardened orthodontic adhesive;

placing the placement device with the appliances on the adhesive dispensing unit in order to transfer unhardened orthodontic adhesive from the adhesive applicators to the base of at least some of the appliances;

detaching the placement device with the appliances from the adhesive dispensing unit while the adhesive remains unhardened;

placing the placement device on the patient's dental arch in order to move the appliances with the respective quantities of unhardened orthodontic adhesive into corresponding positions on the patient's teeth; and hardening the adhesive in order to bond the appliances to the patient's teeth.

2. The method of claim 1 wherein the act of providing an adhesive dispending unit comprises the act of providing a model dental arch having a configuration similar to at least a portion of the patient's dental arch, the model dental arch including a number of model teeth.

3. The method of claim 2 wherein the adhesive applicators are connected to at least some of the model teeth.

4. The method of claim 3 wherein the applicator comprise fibers.

5. The method of claim 3 wherein the applicators include a release surface that comprises a foam material.

6. The method of claim 3 wherein the applicators are resilient.

7. The method of claim 3 wherein the applicators protrude past adjacent portions of surfaces of the model teeth.

8. The method of claim 1 wherein the act of providing a placement device comprises the act of providing an indirect bonding tray.

9. The method of claim 1 wherein the act of providing a placement device comprises the act of providing a jig.

10. The method of claim 1 wherein the act of hardening the adhesive includes the act of directing light toward the adhesive.

11. The method of claim 1 wherein the act of providing an adhesive dispending unit is carried out using software to determine the location of the adhesive applicators.

12. The method of claim 1 wherein the act of releasably connecting a number of orthodontic appliances to the placement device is carried out using software to determine the locations of the appliances on the placement device.

13. The method of claim 1 wherein the act of providing an orthodontic placement device having wall sections that match the configuration of at least a portion of the patient's dental arch is carried out using digital data that is representative of the patient's teeth.

* * * * *